(12) United States Patent
Ganser

(10) Patent No.: US 8,881,599 B2
(45) Date of Patent: Nov. 11, 2014

(54) SPECIMEN HOLDER FOR CLAMPING WORKPIECES

(75) Inventor: Franz Ganser, Laupheim (DE)

(73) Assignee: Zwick GmbH & Co. KG, Ulm (DE)

( * ) Notice: Subject to any disclaimer, the term of this patent is extended or adjusted under 35 U.S.C. 154(b) by 134 days.

(21) Appl. No.: 13/378,509

(22) PCT Filed: Jun. 4, 2010

(86) PCT No.: PCT/DE2010/000640
§ 371 (c)(1),
(2), (4) Date: Feb. 29, 2012

(87) PCT Pub. No.: WO2011/015167
PCT Pub. Date: Feb. 10, 2011

(65) Prior Publication Data
US 2012/0144927 A1    Jun. 14, 2012

(30) Foreign Application Priority Data
Aug. 5, 2009   (DE) .................. 10 2009 036 246

(51) Int. Cl.
*G01N 3/02* (2006.01)
*B23B 31/177* (2006.01)
*G01N 3/04* (2006.01)
*B23B 31/16* (2006.01)

(52) U.S. Cl.
CPC ............. *G01N 3/04* (2013.01); *B23B 31/16254* (2013.01); *G01N 2203/0017* (2013.01); *B23B 31/16287* (2013.01)
USPC .......................................... 73/857

(58) Field of Classification Search
CPC .................. B23B 31/16254; B23B 31/16287; G01N 2203/0017; G01N 3/04
See application file for complete search history.

(56) References Cited

U.S. PATENT DOCUMENTS

| 2,660,440 A | 11/1953 | Kurtz |
| 3,908,449 A * | 9/1975 | Zuber .............................. 73/857 |
| 4,019,378 A | 4/1977 | Keller et al. |
| 6,220,288 B1 * | 4/2001 | Sandau et al. ............. 137/596.2 |

FOREIGN PATENT DOCUMENTS

DE    19816639 A    10/1999

* cited by examiner

*Primary Examiner* — Lisa Caputo
*Assistant Examiner* — Brandi N Hopkins
(74) *Attorney, Agent, or Firm* — Andrew Wilford

(57) ABSTRACT

A test-specimen holder for gripping test specimens to perform material tests in the form of compressive and tensile tests has two grabs coaxially aligned relative to each other and capable of gripping the test specimen. The grabs have angled faces on sides facing away from the test specimen gripped between them. Respective hydraulic gripping cylinders are connected to the grabs for shifting same axially and a wedge can engage the angled faces of both grabs. A fluid-operated synchronization cylinder is connected to the wedge for moving the wedge perpendicular to the axis of the grabs into and out of engagement with the angled faces of the grabs. A fluid reservoir is connected through a 4/2 directional control valve with the gripping cylinders for actuating same. An adjustable first pressure-limiting valve and a check valve connected parallel thereto are connected between the 4/2 valve and the synchronization cylinder.

4 Claims, 2 Drawing Sheets

SPECIMEN HOLDER FOR CLAMPING WORKPIECES

CROSS REFERENCE TO RELATED APPLICATIONS

This application is the US-national stage of PCT application PCT/DE2010/000640 filed 4 Jun. 2010, published 10 Feb. 2011 as WO2011/015167, and claiming the priority of German patent application 102009036246.0 itself filed 5 Aug. 2009.

BACKGROUND OF THE INVENTION

The invention relates to a test-specimen holder for gripping test specimens, in particular, in order to perform material tests in the form of compressive and in particular tensile tests, comprising two grabs that are preferably movable by hydraulic gripping cylinders, are coaxially aligned relative to each other, and grip the test specimen between the grabs.

When test specimens are gripped that are subsequently intended to undergo tensile tests, in particular, it is first of all critical to chuck them on center, that is, on the actual measurement axis, and, second, the test specimens should be chucked over a sufficient length between the grabs so as to prevent as much as possible any twisting torques by the grabs, as can occur with short chucked test specimens. Due to the test specimen geometry, however, it is frequently not possible to effect chucking over a distance of sufficient length. This means that elaborate measures must often be provided so as to ensure that the grabs close symmetrically.

OBJECT OF THE INVENTION

The object of this invention is to create a test-specimen holder of the above-described type in such a way as to ensure that the grabs close symmetrically relative to the measurement axis, and that even short test specimens can be gripped without twisting torques being applied to the grab guides.

SUMMARY OF THE INVENTION

This object is achieved according to the invention by providing both grabs with angled faces on sides facing away from the test specimen, which surfaces contact a wedge that is movable perpendicular to the axis of the grabs and along the test axis by a similarly fluid-operated synchronization cylinder.

The advantage achieved by the invention consists is the fact that the synchronization cylinder, which is fixed relative to the direction of motion of the gripping cylinder and aligned with the measurement axis, along with the wedge ensure that the two grabs close symmetrically relative to each other. To this end, the synchronization cylinder is released to the extent that, although a light counter-pressure is preserved by the wedge so as to maintain the synchronization, the wedge nevertheless retracts and enables both grabs to travel toward the closing position. In particular, when short test specimens are chucked, the synchronization cylinder is released to a predefined extent so that it exerts a specific, definable counter-pressure through the wedge on the grabs, where this counter-pressure is intended to correlate with the gripping pressure of the grabs such that any otherwise occurring twisting torques are just compensated for. The entire process of gripping the test specimen is independent here of the test specimen thickness, and is dynamic during the entire closing and gripping process.

Another advantage is the fact that any play typically present in the grab guides is eliminated by the perpendicularly oriented synchronization cylinder with the wedge. As a result, alternating load tests, in particular, are possible without the travel jumps that typically occur in this connection.

Finally, the entire arrangement is robust in handling overloads, since the synchronization cylinder is simply forced away in the event of overloading such that synchronization is reestablished when the load is released.

In a preferred embodiment of the invention, both gripping cylinders are supplied from a fluid reservoir through a common supply line and through a 4/2 directional control valve. This enables both gripping cylinders to be adjusted essentially uniformly, any design-related and friction-induced imbalances being compensated for by the synchronization cylinder.

Provision is furthermore made within the scope of the invention whereby the synchronization cylinder is connected to the 2/4 directional control valve through an adjustable first pressure-limiting valve and a parallel check valve. This then results in a mode of operation similar to that of a double-acting cylinder that is controlled by a 4/2 or a 5/2 directional control valve, where the stroke is operated at full force in one direction, that is, when gripping, whereas the return stroke can be effected under low pressure. The load on the pressure-limiting valve is thus released by the parallel-connected check valve during return travel.

In addition, a second pressure-limiting valve connected directly to the fluid reservoir can be provided upstream from the 4/2 directional control valve, through which second pressure-limiting valve the contact pressure acting on the grabs can be adjusted in a controlled manner.

Another possible approach provided by the invention consists in making the two pressure-limiting valves work at a fixed pressure ratio relative to each other. This allows an advantageous distribution of force to be adjusted between the grabs on the one hand and the synchronization cylinder on the other hand, even under varying chucking conditions.

The selected angle at which the grabs and the wedge can contact each other can be varied depending on the application; in any case for universal applications within the scope of the invention it has been found advantageous for the angle at which the angled faces of the grabs and the wedge contact each other to be 45°.

BRIEF DESCRIPTION OF THE DRAWING

The following describes the invention in more detail based on an embodiment illustrated in the drawing. Therein.

SPECIFIC DESCRIPTION OF THE INVENTION

Figure 1:
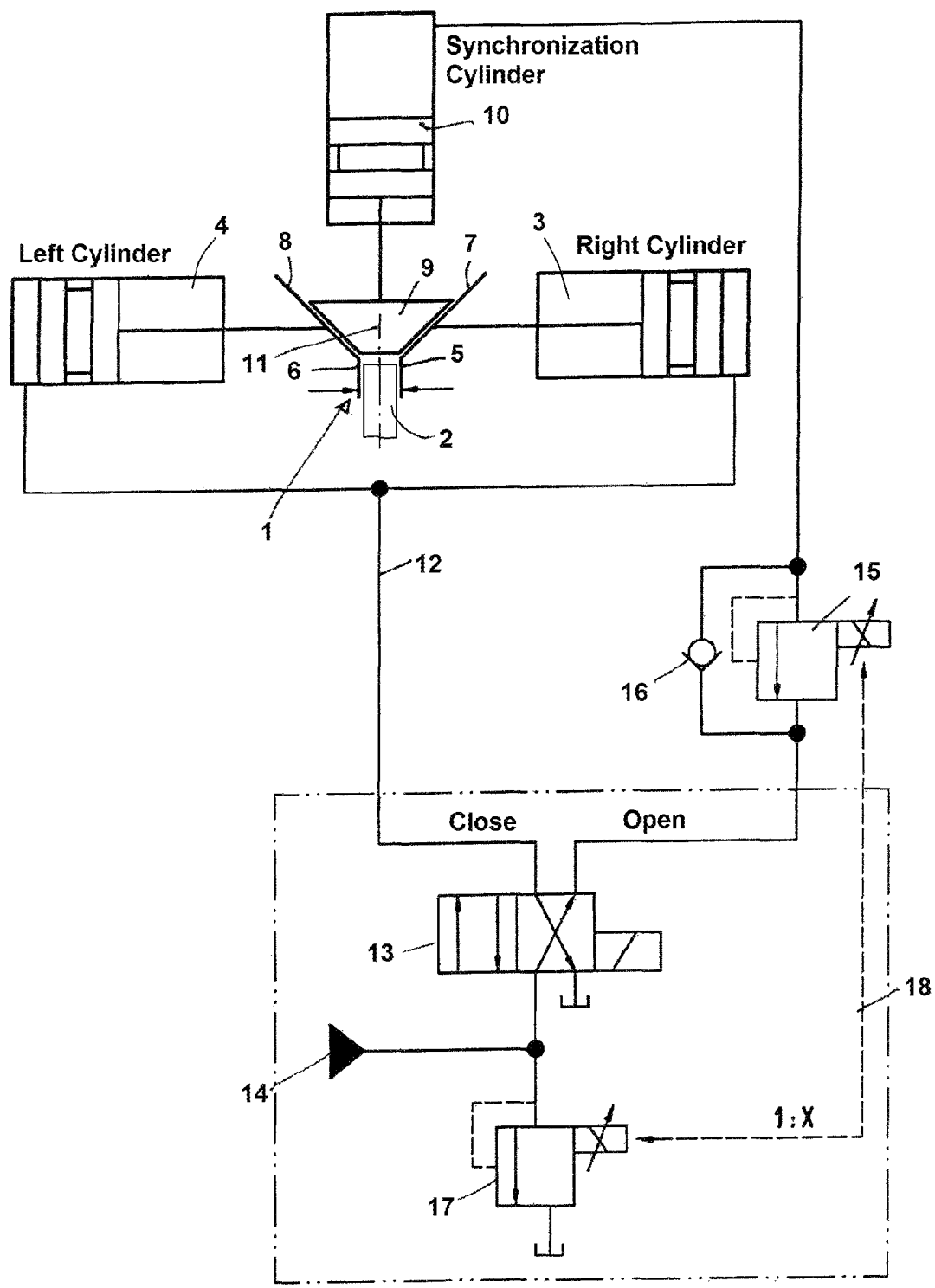
FIG. 1 is a schematic diagram of the test-specimen holder together with the hydraulic equipment controlling it.

The test-specimen holder 1 shown in particular in FIG. 1 functions to grip test specimens 2 to allow component and material tests to be performed in the form of compression and in particular tensile tests.

To this end, the test-specimen holder 1 has two grabs 5 and 6 that are preferably movable by respective hydraulic gripping cylinders 3 and 4 and are oriented coaxially relative to each other to grip the test specimen 2 between them.

On their sides facing away from the test specimen, the grabs 5 and 6 have respective angled faces 7 and 8 that contact a wedge 9. This wedge 9 is also movable perpendicular to the axis of the grabs by a similarly fluid-operated synchronization cylinder 10 and thus toward a test axis 11 of the test specimen 2.

The hydraulic equipment, which is described in detail below and is shown in FIG. 1, ensures that the wedge 9 and grabs 5 and 6 generally remain in mutual contact. This means that the wedge 9 returns back toward the synchronization cylinder 10 when the grabs 5 and 6 close so as to grip the test specimen 2, while the wedge 9 is extended analogously in the opposite direction to open the grabs 5 and 6 and thereby press the grabs 5 and 6 apart.

In order to ensure this motion sequence, both gripping cylinders 3 and 4 are supplied from a fluid reservoir 14 through a common supply line 12 as well as a 4/2 directional control valve 13, the synchronization cylinder 10 also being connected to the 4/2 directional control valve 13 through an adjustable first pressure-limiting valve 15 and a parallel check valve 16.

The result is that this arrangement thus functions like a double-acting cylinder that is similarly controlled by a 4/2 directional control valve.

The pressure-limiting valve 15 in the supply line to the synchronization cylinder 10 together with the check valve 16 enable a mode of operation in which the gripping process proceeds at full high force, while the return stroke is effected at low pressure. The pressure-limiting valve 15 is thus depressurized through the check valve 16 during the return stroke.

In order to enable the contact pressure of the grabs 5 and 6 to be adjusted, a second pressure-limiting valve 17 connected directly to the fluid reservoir 14 is provided upstream from the 4/2 directional control valve 13, through which second directional control valve the pressure in the hydraulic line can be adjusted.

It is furthermore possible for both pressure-limiting valves 15 and 17 to be adjustable at a fixed pressure ratio relative to each other, as is indicated by the broken double arrow 18 in FIG. 1.

In the embodiment of FIG. 1, the selected angle at which the angled faces 7 and 8 of the grabs 5 and 6 and the wedge 9 contact each other is 45°; although in principle it is also possible here to provide both larger and also smaller angles.

Figure 2:
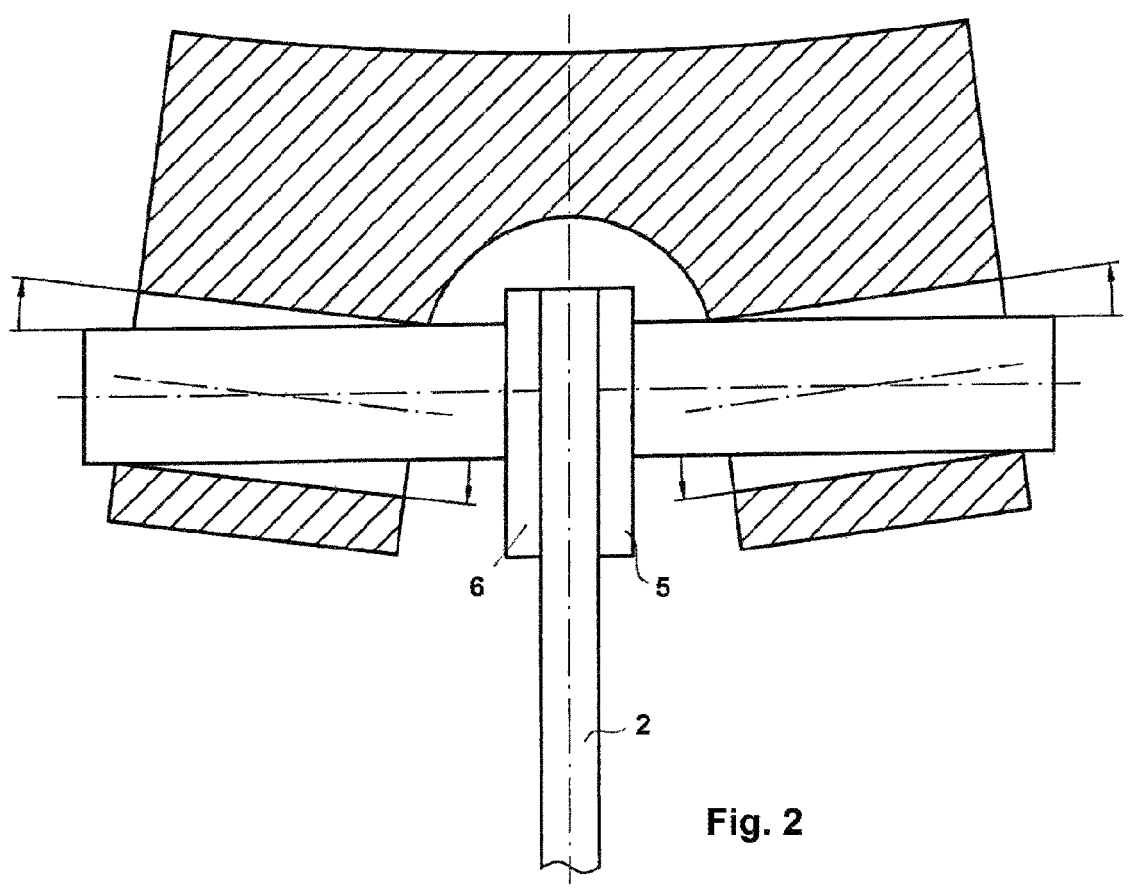
FIG. 2 is a diagram, by way of example, depicting the deformation of the test-specimen holder during the gripping process.

What this gripping device achieves is first of all that both grabs 5 and 6 always close symmetrically, thereby ensuring an automatic alignment of test specimen 2 relative to the measurement axis 11. In addition, travel jumps are prevented that typically occur during alternating-load tests, in particular, due to a twisting motion by grabs 5 and 6, as a result of test-specimen holder deformation effected during the gripping process and of the always present play on the part of the grab guides, as is shown in the exaggerated illustration of FIG. 2. As a result, it is also possible, in particular, to grip extremely short test specimens since the wedge 9 under the pressure of the synchronization cylinder applies the requisite counter-force to prevent any twisting torque on the grab guides.

The invention claimed is:

1. A test-specimen holder for gripping test specimens to perform material tests in the form of compressive and tensile tests, comprising;
    two grabs coaxially aligned relative to each other, and capable of gripping the test specimen between the grabs, the grabs having angled faces on sides facing away from the test specimen gripped between them;
    respective hydraulic gripping cylinders connected to the grabs for shifting same axially;
    a wedge engageable with the angled faces of the grabs;
    a fluid-operated synchronization cylinder connected to the wedge for moving the wedge perpendicular to the axis of the grabs into and out of engagement with the angled faces of the grabs;
    a fluid reservoir;
    a 4/2 directional control valve connected between the fluid reservoir and the gripping cylinders for actuating same; and
    an adjustable first pressure-limiting valve and a check valve connected parallel thereto between the 4/2 valve and the synchronization cylinder.

2. The test-specimen holder according to claim 1, further comprising:
    a second pressure-limiting valve connected directly to the fluid reservoir upstream from the 4/2 directional control valve.

3. The test-specimen holder according to claim 2, wherein both pressure-limiting valves are adjustable at a fixed pressure ratio relative to each other.

4. The test-specimen holder according to claim 1, wherein the angle at which the angled faces of the grabs and the wedge contact each other is 45°.

* * * * *